US012649764B2

(12) United States Patent  
Mattila et al.

(10) Patent No.: US 12,649,764 B2  
(45) Date of Patent: Jun. 9, 2026

(54) METHOD FOR VIRAL INACTIVATION

(71) Applicant: Regeneron Pharmaceuticals, Inc.,  
Tarrytown, NY (US)

(72) Inventors: John Mattila, Nyack, NY (US);  
Andrew Barmasse, Tarrytown, NY  
(US); Mark Chiboroski, Ossining, NY  
(US)

(73) Assignee: REGENERON  
PHARMACEUTICALS, INC.,  
Tarrytown, NY (US)

( * ) Notice: Subject to any disclaimer, the term of this  
patent is extended or adjusted under 35  
U.S.C. 154(b) by 1064 days.

(21) Appl. No.: 17/630,695

(22) PCT Filed: Apr. 23, 2020

(86) PCT No.: PCT/US2020/029468  
§ 371 (c)(1),  
(2) Date: Jan. 27, 2022

(87) PCT Pub. No.: WO2021/021260  
PCT Pub. Date: Feb. 4, 2021

(65) Prior Publication Data  
US 2022/0259261 A1 Aug. 18, 2022

Related U.S. Application Data

(60) Provisional application No. 62/881,692, filed on Aug.  
1, 2019.

(51) Int. Cl.  
*C07K 1/22* (2006.01)  
*C07K 1/36* (2006.01)

(52) U.S. Cl.  
CPC . *C07K 1/22* (2013.01); *C07K 1/36* (2013.01)

(58) Field of Classification Search  
None  
See application file for complete search history.

(56) References Cited

U.S. PATENT DOCUMENTS

| | | | |
|---|---|---|---|
| 2015/0064769 A1 | 3/2015 | Xenopoulos | |
| 2015/0133636 A1 | 5/2015 | Xenopoulos et al. | |
| 2019/0071647 A1 | 3/2019 | Fiadeiro et al. | |

FOREIGN PATENT DOCUMENTS

| | | |
|---|---|---|
| CN | 102711828 A | 10/2012 |
| CN | 103379949 A | 10/2013 |
| CN | 104039825 A | 9/2014 |
| CN | 105017418 A | 11/2015 |
| CN | 106749660 A | 5/2017 |
| CN | 108059650 A | 5/2018 |
| CN | 108342368 A | 7/2018 |
| CN | 109311965 A | 2/2019 |
| EP | 1614693 A1 | 1/2006 |
| EP | 2527429 A2 | 11/2012 |
| WO | 2012135415 A1 | 10/2012 |

OTHER PUBLICATIONS

Pall Corporation "Viral Safety—Practical Solutions for Risk Control" Jun. 1, 2018; 39-page printout. (Year: 2018).*  
Makowiecki, et al. (Genetic Engineering & Biotechnology News, Apr. 15, 2013. (Year: 2013).*  
Fan Bao-qing et al., "Research progress in large-scale antibody drug production and purification technology", Chemistry and Bioengineering, 2018, vol. 35, Issue 10 (6 pages).  
Alice R. Mazzer et al., "Protein A chromatography increases monoclonal antibody aggregation rate during subsequent low pH virus inactivation hold", J Chromatogr A. Oct. 9, 2015; 1415: 83-90 (20 pages).  
Pall Corporation, "Viral Safety—Practical Solutions for Risk Control," Jun. 1, 2018, pp. 1-39.  
Makowiecki, J., "Adjusting pH During Viral Inactiviation," Genetic Engineering & Biotechnology News, Apr. 15, 2013.  
Ishihara et al.: "Accelerated purification process development of monoclonal antibodies for shortening time to clinic," Journal of Chromatography, vol. 1176, No. 1-2, Nov. 7, 2007, pp. 149-156.  
International Search Report for PCT/US2020/029468, dated Jul. 21, 2020 (3 pages).  
J. Mattila et al., "Retrospective Evaluation of Low-pH Viral Inactivation and Viral Filtration Data from a Multiple Company Collaboration", PDA J. Pharm Sci. Technol., 2016, vol. 70, No. 3, pp. 293-299.

* cited by examiner

*Primary Examiner* — Benjamin P Blumel  
*Assistant Examiner* — Jeffrey Mark Sifford  
(74) *Attorney, Agent, or Firm* — BakerHostetler

(57) ABSTRACT

Embodiments of the present disclosure are directed to systems and methods for modulating pH in a mixture containing a polypeptide. The pH may be modulated for any suitable purpose, e.g., inactivating virus in the mixture. Methods may include eluting, from a chromatography column, a mixture (e.g., an eluate) having a pH greater than, e.g., 3.9 and less than, e.g., 8.5. Methods may further include one or more of measuring a protein concentration of the mixture and measuring a pH of the mixture. An amount of acid necessary to reduce the pH of the mixture to a target pH may then be calculated based on the protein concentration of the mixture, the pH of the mixture, or both. After an acid addition amount is calculated, a portion of acid may be added to the mixture, wherein the portion of acid is sufficient to achieve the target pH.

29 Claims, 3 Drawing Sheets

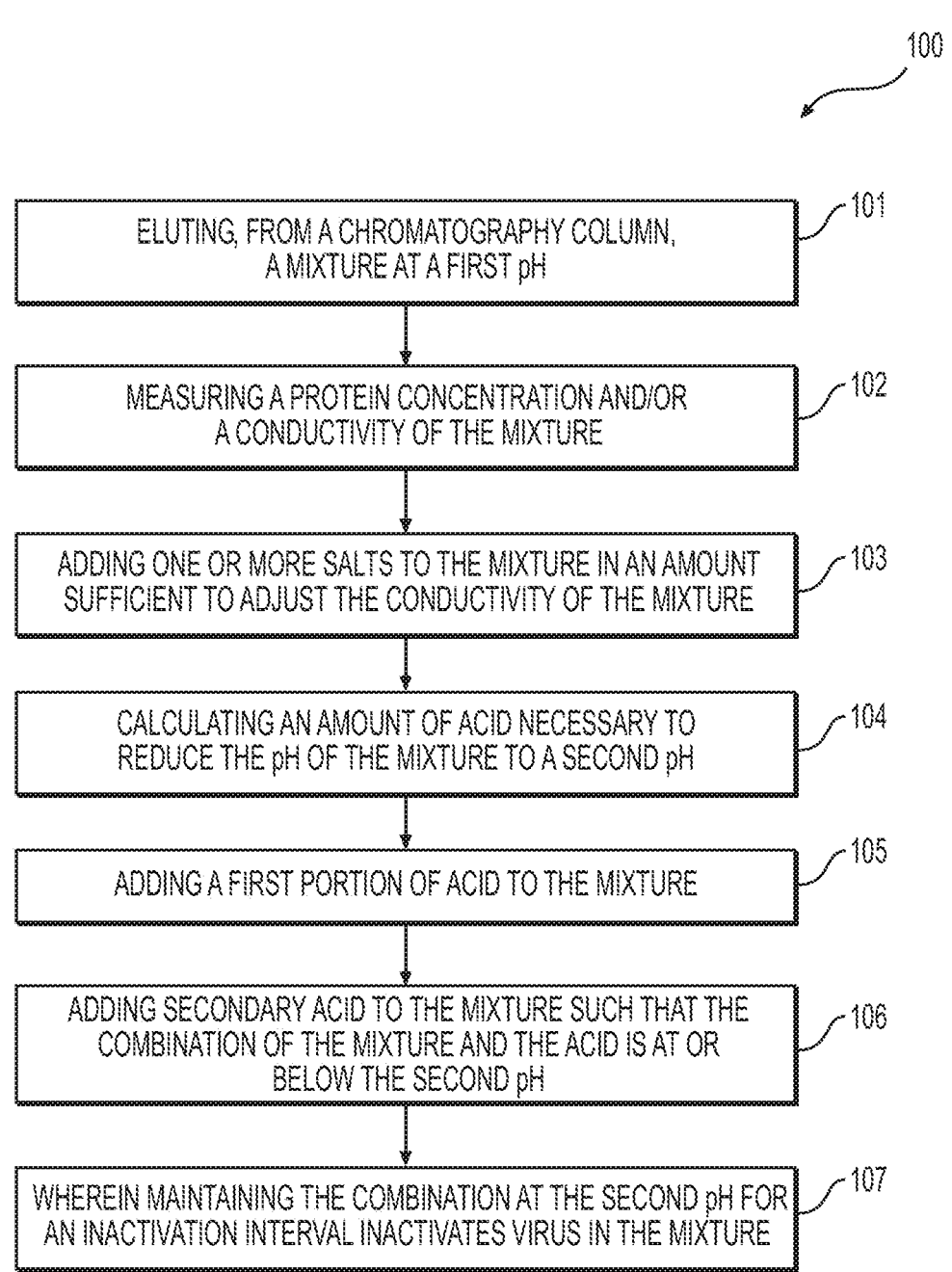

100

101
ELUTING, FROM A CHROMATOGRAPHY COLUMN, A MIXTURE AT A FIRST pH

102
MEASURING A PROTEIN CONCENTRATION AND/OR A CONDUCTIVITY OF THE MIXTURE

103
ADDING ONE OR MORE SALTS TO THE MIXTURE IN AN AMOUNT SUFFICIENT TO ADJUST THE CONDUCTIVITY OF THE MIXTURE

104
CALCULATING AN AMOUNT OF ACID NECESSARY TO REDUCE THE pH OF THE MIXTURE TO A SECOND pH

105
ADDING A FIRST PORTION OF ACID TO THE MIXTURE

106
ADDING SECONDARY ACID TO THE MIXTURE SUCH THAT THE COMBINATION OF THE MIXTURE AND THE ACID IS AT OR BELOW THE SECOND pH

107
WHEREIN MAINTAINING THE COMBINATION AT THE SECOND pH FOR AN INACTIVATION INTERVAL INACTIVATES VIRUS IN THE MIXTURE

FIG. 1

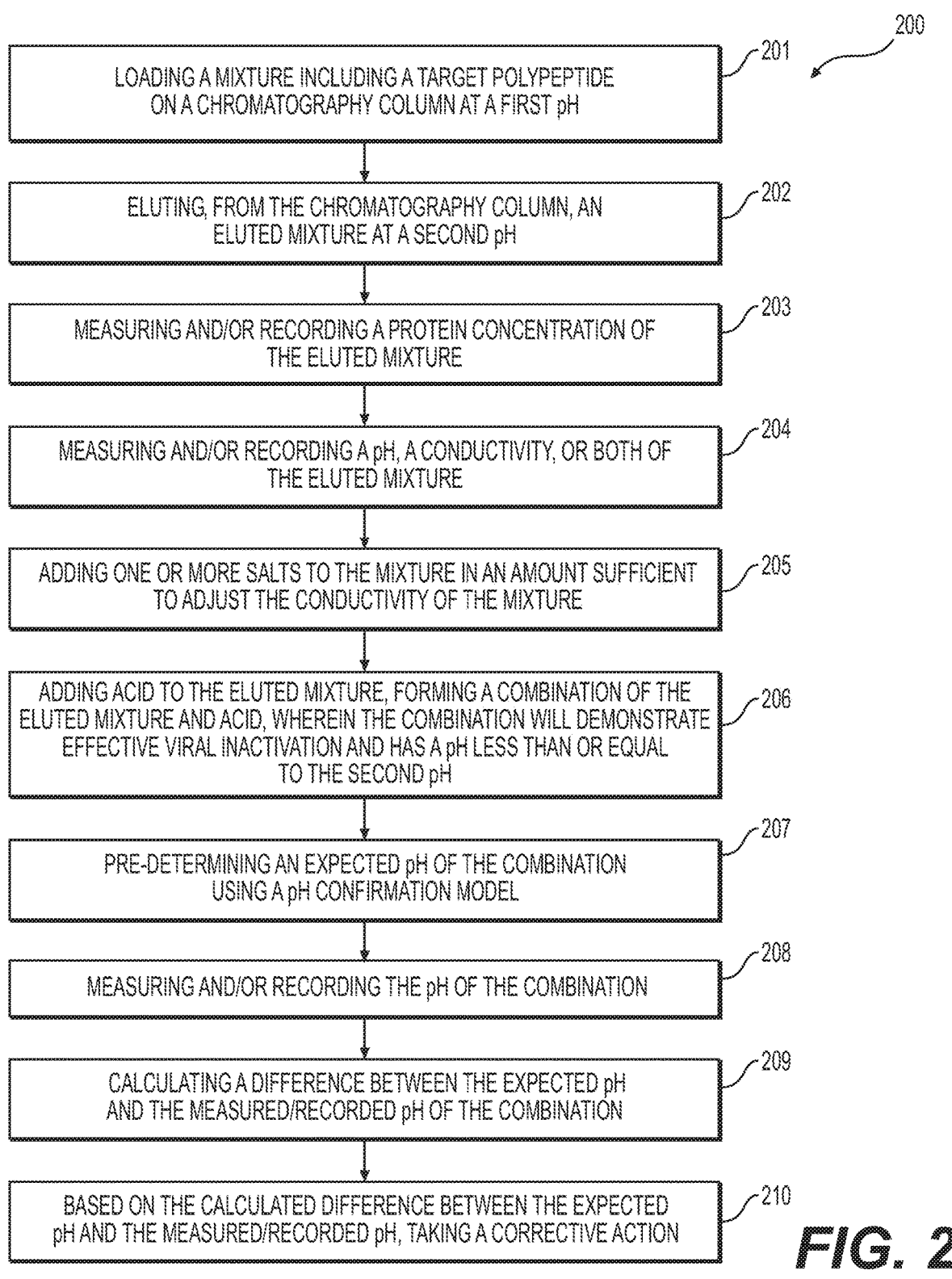

LOADING A MIXTURE INCLUDING A TARGET POLYPEPTIDE
ON A CHROMATOGRAPHY COLUMN AT A FIRST pH ⟋201

ELUTING, FROM THE CHROMATOGRAPHY COLUMN, AN
ELUTED MIXTURE AT A SECOND pH ⟋202

MEASURING AND/OR RECORDING A PROTEIN CONCENTRATION OF
THE ELUTED MIXTURE ⟋203

MEASURING AND/OR RECORDING A pH, A CONDUCTIVITY, OR BOTH OF
THE ELUTED MIXTURE ⟋204

ADDING ONE OR MORE SALTS TO THE MIXTURE IN AN AMOUNT SUFFICIENT
TO ADJUST THE CONDUCTIVITY OF THE MIXTURE ⟋205

ADDING ACID TO THE ELUTED MIXTURE, FORMING A COMBINATION OF THE
ELUTED MIXTURE AND ACID, WHEREIN THE COMBINATION WILL DEMONSTRATE
EFFECTIVE VIRAL INACTIVATION AND HAS A pH LESS THAN OR EQUAL
TO THE SECOND pH ⟋206

PRE-DETERMINING AN EXPECTED pH OF THE COMBINATION
USING A pH CONFIRMATION MODEL ⟋207

MEASURING AND/OR RECORDING THE pH OF THE COMBINATION ⟋208

CALCULATING A DIFFERENCE BETWEEN THE EXPECTED pH
AND THE MEASURED/RECORDED pH OF THE COMBINATION ⟋209

BASED ON THE CALCULATED DIFFERENCE BETWEEN THE EXPECTED
pH AND THE MEASURED/RECORDED pH, TAKING A CORRECTIVE ACTION ⟋210

METHOD FOR VIRAL INACTIVATION

CROSS-REFERENCE TO RELATED APPLICATION

This application is a U.S. national stage filing under 35 U.S.C. § 371 of International Application No. PCT/US2020/029468, filed Apr. 23, 2020, which claims priority to U.S. Provisional Patent Application No. 62/881,692, filed Aug. 1, 2019, the entire disclosure of which is hereby incorporated by reference in its entirety.

TECHNICAL FIELD

This disclosure generally relates to methods for achieving a target pH in a mixture containing a polypeptide. More specifically, this disclosure relates to methods for achieving a target pH in a mixture containing a polypeptide, to assist in ensuring that enveloped viruses or virus-like particles are inactivated.

BACKGROUND

In the manufacture of polypeptides, a target molecule (e.g., a target polypeptide component of a drug product) may be separated from a culture medium. Separation processes such as, for example, affinity chromatography and the like, may be performed as a part of target molecule preparation processes. After such separation processes, the resulting mixture containing the polypeptide may potentially include undesirable viruses, or other contaminants undesirable for inclusion in a drug product. Methods of removing or inactivating such contaminants are therefore desirable.

In some commercial scale target molecule synthesis processes, Process Analytical Technology (PAT) may be implemented. PAT includes systems and methods involved in the design, analysis, and control of manufacturing processes of target molecules. PAT includes identifying process parameters which affect qualities of products and periodically monitoring the parameters to ensure the qualities of the products are maintained. PAT is encouraged by regulatory bodies to generally lower risks associated with target molecules and drug products. PAT may provide statistical validation or confirmation that one or more process conditions are met that may improve or maintain a quality of a target molecule and/or product.

The methods and systems disclosed herein may improve the efficiency and/or productivity of polypeptide preparation methods including viral inactivation. Methods and systems disclosed herein may also improve the efficiency and/or productivity of drug product preparation methods and may address one or more problems identified above.

SUMMARY

Embodiments of the present disclosure may be directed to a method for inactivating a virus in a mixture, e.g., an eluate. The method may include eluting, from a chromatography column, the mixture at a pH greater than 3.9 and less than 8.5. The method may further include measuring a protein concentration of the mixture and measuring a pH of the mixture. An amount of acid necessary to reduce the pH of the mixture to an inactivation pH may then be calculated based on the protein concentration of the mixture. After an acid addition amount is calculated, a first portion of acid may be added to the mixture, wherein the first portion of acid is 68% to 99% of the acid addition amount. The method may further include adding an additional portion of acid to the mixture such that the pH of the mixture is at or below the inactivation pH. In methods of the present disclosure, a mixture may be maintained at the inactivation pH for an inactivation interval, configured to inactivating a virus in the mixture.

In some embodiments of the present disclosure, a method for inactivating a virus in a mixture may include loading a mixture including a target molecule on a chromatography column, the loading occurring at a pH greater than or equal to approximately 5.0 and less than or equal to approximately 8.5. The method may further include eluting, from the chromatography column, an eluted mixture including the target molecule at a pH greater than approximately 3.9 and less than or equal to approximately 5.0. The method may also include adding acid to the mixture, forming a combination of the mixture and acid, wherein the combination is configured to demonstrate effective viral inactivation and the combination has a pH less than or equal to approximately 3.8 and greater than or equal to approximately 3.0. An expected pH of the combination may be pre-determined using a pH confirmation model. Further, the pH of the combination may be measured and/or recorded. A difference between the expected pH to the recorded pH may be calculated, and based on the calculated difference between the expected pH and the recorded pH, a corrective action may be taken.

Further embodiments of the present disclosure may include a method for developing an acidic inactivation protocol. The method may include producing a pool of eluates, wherein each eluate of the pool of eluates contains a target molecule purified in a protein affinity capture process. The method may include measuring the pH and/or protein concentration of each eluate of the pool of eluates. Further, each eluate of the pool of eluates may be titrated to determine an amount of acid needed to bring the eluate to an inactivation pH. A relationship may then be regressed between the amount of acid added, eluate protein concentration, eluate pH, and inactivation pH.

In some embodiments of the present disclosure, a method for inactivating virus in a mixture may include measuring a protein concentration of the mixture. An amount of acid necessary to reduce the pH of the mixture to an inactivation pH may then be calculated based on the protein concentration of the mixture. After an acid addition amount is calculated, the amount of acid necessary to reduce the pH of the mixture may be added to the mixture.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments. Any features of an embodiment or example described herein (e.g., composition, formulation, method, etc.) may be combined with any other embodiment or example, and all such combinations are encompassed by the present disclosure. Moreover, the described systems and methods are neither limited to any single aspect nor embodiment thereof, nor to any combinations or permutations of such aspects and embodiments. For the sake of brevity, certain permutations and combinations are not discussed and/or illustrated separately herein.

FIG. 1 depicts, in flow-chart form, an exemplary process for inactivating virus in an eluate, according to the present disclosure;

FIG. 2 depicts, in flow-chart form, an exemplary process for inactivating virus in an eluate, according to the present disclosure.

Figure 3:
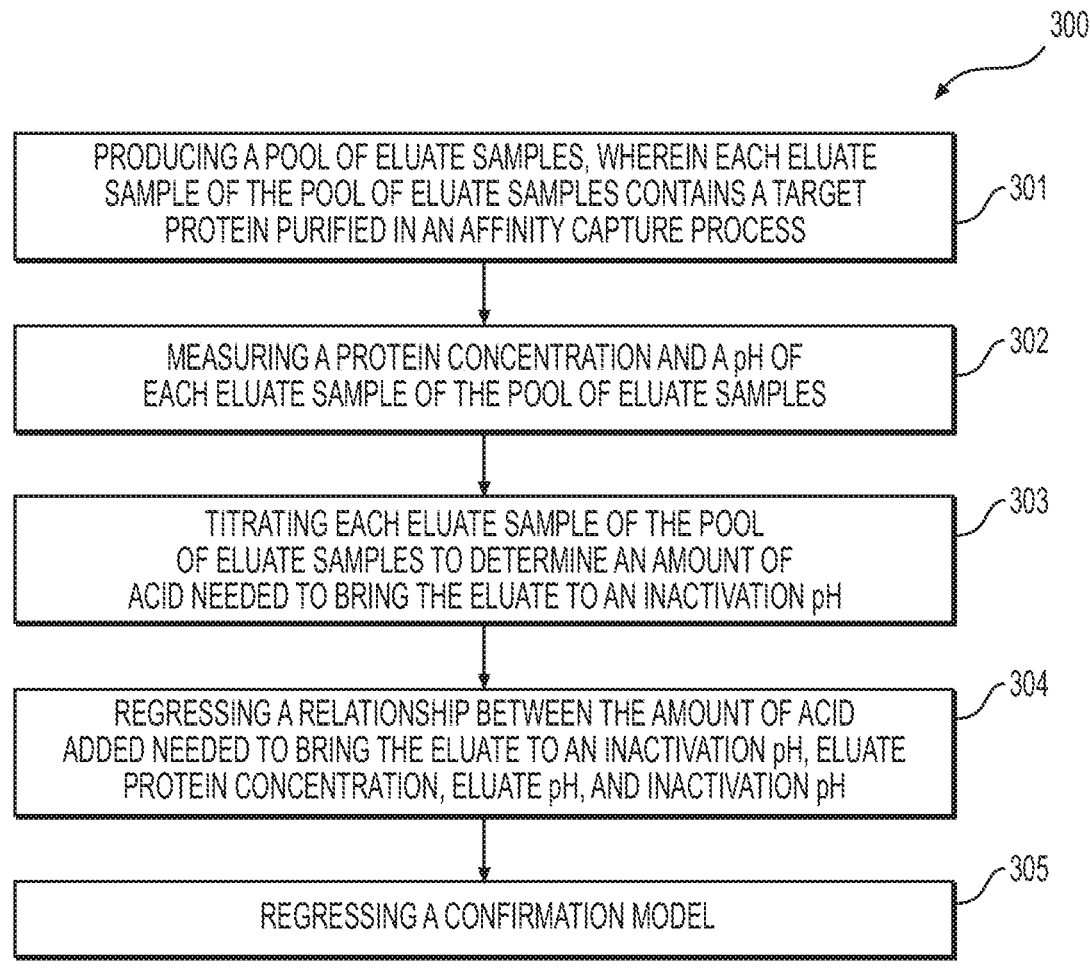
FIG. 3 depicts, in flow-chart form, an exemplary process for developing an acidic inactivation protocol, according to the present disclosure.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." For the terms "for example" and "such as," and grammatical equivalences thereof, the phrase "and without limitation" is understood to follow unless explicitly stated otherwise.

As used herein, the term "about" is meant to account for variations due to experimental error. When applied to numeric values, the terms "about" and "approximately" may indicate a variation of +/−5% from the disclosed numeric value, unless a different variation is specified. When applied to pH values, the terms "about" and "approximately" may indicate a variation of +/−0.05. As used herein, the singular forms "a," "an," and "the" include plural referents unless the context clearly dictates otherwise.

It should be noted that all numeric values disclosed herein (including all disclosed values, limits, and ranges) may have a variation of +/−5% from the disclosed numeric value unless a different variation is specified. pH values disclosed herein may have a variation of +/−0.05. Further, all ranges are understood to be inclusive of endpoints, e.g., from 1 centimeter (cm) to 5 cm would include lengths of 1 cm, 5 cm, and all distances between 1 cm and 5 cm.

DETAILED DESCRIPTION

This disclosure is not limited to the particular compositions, formulations, material manufacturers, drug products, devices, systems, experimental conditions, or specific methods disclosed herein, as many variations are possible within the purview of one of ordinary skill in the art. The terminology used herein is for the purpose of describing particular embodiments only, and is not intended to be limiting.

Unless defined otherwise, all technical and scientific terms used herein have the same meaning as is commonly understood by one of ordinary skill in the art to which this disclosure belongs. Although any suitable methods and materials (e.g., similar or equivalent to those described herein) can be used in the practice or testing of the present disclosure, particular methods are now described. All publications mentioned are hereby incorporated by reference.

The term "polypeptide" as used herein refers to any amino acid polymer having more than about 20 amino acids covalently linked via amide bonds. Proteins contain one or more amino acid polymer chains (e.g., polypeptides). Thus, a polypeptide may be a protein, and a protein may contain multiple polypeptides to form a single functioning biomolecule.

Post-translational modifications may modify or alter the structure of a polypeptide. For example, disulfide bridges (e.g., S—S bonds between cysteine residues) may be formed post-translationally in some proteins. Some disulfide bridges are essential to proper structure, function, and interaction of polypeptides, immunoglobulins, proteins, co-factors, substrates, and the like. In addition to disulfide bond formation, proteins may be subject to other post-translational modifications, such as lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). Post-translational modifications may affect the hydrophobicity, electrostatic surface properties, or other properties which determine the surface-to-surface interactions participated in by the polypeptide.

As used herein, the term "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, antibody-like molecules, nanobodies, recombinant antibody chimeras, cytokines, chemokines, peptide hormones, and the like. A protein-of-interest (POI) may include any polypeptide or protein that is desired to be isolated, purified, or otherwise prepared. POIs may include target polypeptides or other polypeptides produced by a cell, including antibodies.

The term "antibody," as used herein, includes immunoglobulins comprised of four polypeptide chains: two heavy (H) chains and two light (L) chains inter-connected by disulfide bonds. Typically, antibodies have a molecular weight of over 100 kDa, such as between 130 kDa and 200 kDa, such as about 140 kDa, 145 kDa, 150 kDa, 155 kDa, or 160 kDa. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3.

A class of immunoglobulins called Immunoglobulin G (IgG), for example, is common in human serum and comprises four polypeptide chains—two light chains and two heavy chains. Each light chain is linked to one heavy chain via a cystine disulfide bond, and the two heavy chains are bound to each other via two cystine disulfide bonds. Other classes of human immunoglobulins include IgA, IgM, IgD, and IgE. In the case of IgG, four subclasses exist: IgG 1, IgG 2, IgG 3, and IgG 4. Each subclass differs in their constant regions, and as a result, may have different effector functions. In some embodiments described herein, a POI may comprise a target polypeptide including IgG. In at least one embodiment, the target polypeptide comprises IgG 4.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Target molecules (e.g., target polypeptides) may be produced using recombinant cell-based production systems, such as the insect bacculovirus system, yeast systems (e.g., *Pichia* sp.), or mammalian systems (e.g., CHO cells and CHO derivatives like CHO-K1 cells). The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, bacculovirus-infected insect cells, Trichoplusiani, etc.), non-human animal cells, human cells, or cell fusions such as, for example, hybridomas or quadromas. In some embodiments a cell may be a human, monkey, ape, hamster, rat, or mouse cell. In some embodiments, a cell may be eukaryotic and may be selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, a cell may comprise one or more viral genes, e.g. a retinal cell that expresses a viral gene (e.g., a PER.C6™ cell).

The term "target molecule" may be used herein to refer to target polypeptides (e.g., antibodies, antibody fragments, or other proteins or protein fragments), or to other molecules intended to be produced, isolated, purified, and/or included in drug products (e.g., adeno-associated viruses (AAVs) or other molecules for therapeutic use). While methods according to the present disclosure may refer to target polypeptides, they may be as applicable to other target molecules. AAVs, for example, may be prepared according to suitable methods (e.g., depth filtration, affinity chromatography, and the like), and mixtures including AAVs (e.g., eluates including AAVs) may be subjected to methods according to the present disclosure. Before or after following one or more methods of the present disclosure, mixtures including AAVs may be subjected to additional procedures (e.g., to the removal of "empty cassettes" or AAVs that do not contain a target sequence).

The term "viral content" refers to a qualitative description of a mixture. For example, if a mixture contains viruses or virus-like particles, that mixture has viral content. In some embodiments, viral content may be quantified in terms of number of virus particles or number of infectious units per volume of mixture (i.e., a concentration). The term "viral concentration" may refer to a concentration of virus particles (e.g., active and inactive virus particles) or a concentration of infectious units.

An exemplary method for viral inactivation may include the addition of acid to a mixture in order to achieve a pH known to inactivate some virus and virus-like particles, and holding the mixture at the achieved pH for a predetermined amount of time. For example, in some embodiments, methods herein may inactivate retroviruses and retrovirus-like particles. In some embodiments, a method for preparing a target molecule from a mixture including the target molecule may comprise contacting the mixture to a chromatography apparatus. Such chromatography apparatuses may include pre-manufactured apparatuses (e.g., Cadence™ BioSMB (Pall Biosciences), BioSC® (novasep), Varicol® (novasep), or Octave (Semba® Biosciences)), custom manufactured apparatuses, hand-assembled apparatuses, or merely two or more standard batch chromatography apparatuses used in tandem.

In some embodiments, target molecule may be eluted from a chromatography apparatus by contacting a stripping buffer to a chromatography apparatus (e.g., a chromatography column), and/or contacting an equilibration buffer to the chromatography apparatus. In some embodiments, a stripping buffer may comprise water, an alkaline solution, or a solution comprising alcohol. Water, such as deionized water, for example, may have less than 5 percent by volume (vol. %) dissolved ions, less than 1 vol. % dissolved ions, less than 0.1 vol. % dissolved ions, or even less than 0.01 vol. % dissolved ions. According to some embodiments, an alkaline solution may comprise one or more alkaline ionic compounds such as $LiOH$, $NaOH$, $KOH$, $Ca(OH)_2$, $NH_4OH$ or other alkaline compound. The concentration of alkaline compound in the stripping buffer may range, for example, from about 0.1 N to about 1.5 N, from about 0.1 N to about 1 N, from about 0.1 N to about 1.5 N, from about 0.5 N to about 1.5 N, from about 0.1 N to about 0.8 N, from about 0.1 N to about 0.6 N, from about 0.1 N to about 0.5 N, from about 0.1 N to about 0.4 N, or from about 0.1 N to about 0.3 N. For example, the concentration of alkaline compound in the stripping buffer may be about 0.1 N, about 0.2 N, about 0.3 N, about 0.4 N, about 0.5 N, about 0.6 N, about 0.7 N, about 0.8 N, about 0.9 N, about 1 N, about 1.1 N, about 1.2 N, about 1.3 N, about 1.4 N, or about 1.5 N. A stripping buffer comprising alcohol may include methanol, ethanol, propanol, benzyl alcohol, or other alcohol. The concentration of alcohol in the stripping buffer may range from about 0.1 vol. % to about 30 vol. %, such as from about 0.5 vol. % to about 30 vol. %, from about 0.5 vol. % to about 25 vol. %, from about 0.5 vol. % to about 25 vol. %, from about 0.5 vol. % to about 25 vol. %, from about 1 vol. % to abut 20 vol. %, from about 1 vol. % to about 15 vol. %, from about 1 vol. % to about 10 vol. %, from about 10 vol. % to about 50 vol. %, from about 10 vol. % to about 40 vol. %, from about 10 vol. % to about 30 vol. %, from about 10 vol. % to about 25 vol. %, from about 15 vol. % to about 25 vol. %, or from about 20 vol. % to about 25 vol. %, based on the total weight of the stripping buffer. For example, the concentration of alcohol in the stripping buffer may be about 0.1 vol. %, about 0.5 vol. %, about 1 vol. %, about 2 vol. %, about 3 vol. %, about 5 vol. %, about 10 vol. %, about 15 vol. %, about 20 vol. %, or about 25 vol. %.

In some embodiments, an equilibration buffer may be similar or identical in composition to the stripping buffer. In other embodiments, the equilibration buffer may vary in composition compared to the stripping buffer. In some embodiments, the equilibration buffer may comprise one or more salts such as, for example, sodium, potassium, magnesium, calcium, citrate, acetate, phosphate, sulfate, Tris, or other salt.

In one or more embodiments, a method for viral inactivation may be employed after a mixture including a target molecule is eluted from a chromatography apparatus (e.g., a packed bed affinity chromatography column, a hydrophobic-interaction chromatography column, an ion-exchange chromatography column, and/or a size-exclusion chromatography column). The loading of a target molecule into the chromatography apparatus may vary dependent on upstream processes, while the mixture containing the target molecule may be eluted from the chromatography apparatus at a constant volume. In some embodiments, the mixture including the target molecule is loaded onto a chromatography column at a pH greater than or equal to approximately 5.0 and less than or equal to approximately 8.5, such as, for example, greater than or equal to approximately 5.5 and less than or equal to approximately 8.5, greater than or equal to approximately 6.0 and less than or equal to approximately 8.5, or approximately 5.0 to approximately 6.5. As a result of the variations in loading, the protein concentration and/or pH of the eluate (e.g., the eluate eluted from the chromatography apparatus) may vary. Due to this variation, the amount of acid that is required to be added for viral inactivation also varies.

In conventional manufacturing processes, low pH viral inactivation is accomplished via a trial and error methodology, where a predetermined amount of acid is added to the eluate, the pH of the eluate and acid mixture is measured, and the addition and measurement steps are continued iteratively until an inactivation pH is reached. Due to the potential costs and losses that can accrue from the addition of too much acid, such processes are conservative and involve small acid addition amounts and long inactivation process times, often on the scale of hours.

Aspects of the present disclosure may provide various benefits to the process of preparing a target polypeptide or other target molecule. For example, one or more methods and/or mathematical models described herein may be implemented to determine an acid addition amount, e.g., the amount of acid required to bring a mixture (containing the target molecule and, potentially, unwanted virus or virus-like particles) to an inactivation pH. An amount of acid approximately equivalent to the acid addition amount may be added to the mixture. As described in greater detail below, the amount of acid equivalent to the acid addition amount may be added as a single bolus or in two or more administrations of acid. The administration of acid for viral inactivation in this fashion may be more efficient and less susceptible to error than conventional trial and error methodologies.

In some aspects of the present disclosure, as a part of a process, a viral content or content of infectious units in a mixture may be known or expected to be minimal or non-existent. In some such aspects of the present disclosure, systems and methods disclosed herein advantageously may be incorporated into a manufacturing process as a part of PAT, to, e.g., decrease potential variabilities within a process, provide real-time confirmation of adherence to process standards, and/or increase confidence in the integrity of a process.

Additional benefits and advantages of aspects of the present disclosure will be apparent to those of ordinary skill in the art.

As alluded to previously, after a target molecule is prepared using one or more chromatography and/or separation processes, a mixture (e.g., an eluate) may be obtained. In some embodiments, one or more measurements may be taken of the mixture, including, e.g., protein concentration, target molecule concentration, pH, or a combination thereof. Protein concentration may be measured by any suitable method, including, e.g., by ultraviolet/visible light spectroscopy. In some embodiments, protein concentration is measured using a wavelength characteristically absorbed by the target molecule, which may be a polypeptide. In such embodiments, the overall protein concentration may be approximately equivalent to the concentration of target molecule (e.g., target polypeptide). In some embodiments, a mixture including the target molecule may have a protein concentration of approximately 7.0 grams of protein per liter of eluate (g/L) to approximately 35.0 g/L, greater than or equal to 7.0 g/L, less than or equal to approximately 20.0 g/L, approximately 8.5 g/L to approximately 18.5 g/L, or approximately 10.0 g/L to approximately 17.0 g/L.

The pH of the mixture may be measured by any suitable method. Accurate and consistent measurement of pH is important for the successful inactivation of viral proteins by low pH. Measurements of pH may be affected by temperature, type of pH probe used, individual differences between pH probes of the same type, and/or physical interactions between the measured medium and the pH probe. Even in standardized pH measuring processes, variation of ±0.05 pH may be common. In the fields of polypeptide manufacture or viral inactivation, variations on the scale of ±0.05 pH may represent about 20% of the working pH range and may deleteriously affect viral inactivation and/or process validation. Such variations may even compound over time, leading to instrument drift and more extreme variation in pH measurements. Thus, in some embodiments, variations in pH measurement may be taken into account when measuring pH. In some embodiments, as alluded to, the pH of the eluate may be measured by a standardized method, with the goal of reducing or eliminating variability in pH measurements. Standardization of a pH measurement method may include using a single manufacturer of pH probes, using a single lot of pH probes, measuring pH at a predetermined temperature, standardizing a measurement sample matrix, and the like. In some embodiments, the pH of the eluate may be measured by a pH meter, such as, for example, a potentiometric pH meter. In some embodiments, the eluate including target molecule may have a pH greater than or equal to approximately 3.9 and less than or equal to approximately 8.5, such as, for example, approximately 3.9 to approximately 6.5, approximately 3.9 to approximately 5.5, approximately 4.5 to approximately 6.5, approximately 4.0 to approximately 4.4, approximately 3.9 to approximately 4.4, or approximately 4.0 to approximately 4.3. As used herein, a pH value, or a range of pH values, may have a variation of ±0.05 pH units.

The presence of some viruses and virus-like particles (e.g., enveloped viruses, retroviruses, retrovirus-like particles, pseudorabies, Herpes viruses, etc.) in mixtures (e.g., eluates), formulations, and/or drug products may affect the components, characteristics, or usability of such mixtures, formulations, and/or drug products. For example, the presence of unwanted viruses or virus-like particles in a drug product may affect product stability, reduce a product's shelf life, or result in the product's failure to meet internal, compendial or regulatory (e.g., U.S. Food & Drug Administration) specifications. Some virus or virus-like particles may cause clinical effects, such as an immunogenic reaction upon administration of a drug product including a virus. Embodiments of the present disclosure may be useful in inactivating virus or virus-like particles to decrease or eliminate any or all such undesirable effects. For example, embodiments of the present disclosure may be applicable to mixtures (e.g., eluates) having viral content following one or more polypeptide purification processes (e.g., a separation process including a protein A affinity column).

In some embodiments, prior to viral inactivation, a conductivity of the mixture may be measured. In some embodiments, one or more salts may be added to a mixture to adjust its conductivity (e.g., increase conductivity) prior to viral inactivation. The one or more salts may include alkali metal salts, alkali earth metal salts, halides, and/or one or more other ionoactive compounds. Without being limited by theory, addition of one or more salts to adjust conductivity may reduce aggregation of target molecules, viruses or retrovirus-like particles. The aggregation of target molecules, viruses or retrovirus-like particles may affect how surfaces of these species interact with acid. The addition of salts to a mixture may increase the ionic activity of the mixture, increase conductivity of the mixture, and decrease target molecule or virus aggregation. Therefore, in some embodiments, the conductivity of a mixture may be related to the degree of aggregation of target molecules or viruses.

In some cases, embodiments of the present disclosure may be applicable to mixtures with an extremely low viral content (e.g., less than or equal to approximately 0.0001 viral particles or infectious units per mL), or even a non-existent viral content. Chromatography and other separation processes, alone or in combination, may adequately purify and/or separate a target molecule and remove unwanted viruses or virus-like particles from a mixture. In some such cases, methods according to the present disclosure may be beneficial to serve as additional assurance that virus or virus-like particles are inactivated, and to ensure product stability, product safety, product effectiveness, and compliance with internal or regulatory specifications. Thus, embodiments of the present disclosure may also be applicable to mixtures without any known viral content in order to, for example, ensure regulatory guidelines are met and/or provide redundant quality control.

The viral inactivation protocols and methods described herein may be implemented without adversely affecting certain types of viruses, such as AAVs (e.g., an AAV including a target sequence). For example, advantageously, protocols and methods described herein may be performed without degrading AAVs. Thus, methods described herein may be suitable for use in mixtures containing an AAV as a target molecule.

As alluded to previously, viruses in a mixture may be inactivated by holding the mixture at an inactivation pH for an inactivation interval. The inactivation pH may be a pH less than or equal to 3.8 and greater than or equal to 3.0, such as, for example, a pH of 3.35 to 3.8, less than or equal to 3.75 and greater than or equal to 3.0, less than or equal to 3.7 and greater than or equal to 3.0, less than or equal to 3.65 and greater than or equal to 3.0, less than or equal to 3.6 and greater than or equal to 3.0, less than or equal to 3.55 and greater than or equal to 3.0, less than or equal to 3.5 and greater than or equal to 3.0, less than or equal to 3.45 and greater than or equal to 3.0, less than or equal to 3.4 and greater than or equal to 3.0, 3.35 to 3.75, 3.5 to 3.8, 3.5 to 3.75, 3.5 to 3.7, 3.5 to 3.6, or 3.5 to 3.65. As used herein, a pH value, or a range of pH values, may have a variation of ±0.05 pH units. If an inactivation pH is set too high, there is a risk of variation within the process allowing for insufficient viral inactivation. If an inactivation pH is set too low, there is a risk of denaturing the target molecule or other proteins, or otherwise altering the mixture in an undesirable manner.

The inactivation interval describes the interval of time during which the mixture is held at the inactivation pH. The inactivation interval may be approximately 20 minutes to approximately 90 minutes, such as, for example, approximately 30 minutes, approximately 45 minutes, approximately 60 minutes, approximately 30 minutes to approximately 45 minutes, approximately 30 minutes to approximately 60 minutes, approximately 30 minutes to approximately 75 minutes, approximately 30 minutes to approximately 90 minutes, approximately 45 minutes to approximately 60 minutes, approximately 45 minutes to approximately 75 minutes, approximately 45 minutes to approximately 90 minutes, approximately 60 minutes to approximately 75 minutes, or approximately 60 minutes to approximately 95 minutes. Holding the mixture at an inactivation pH for an inactivation interval may reduce, eliminate, or ensure the absence of viral activity in the mixture. The low pH environment may denature viral proteins, such as, for example, viral envelope proteins. The denatured viral proteins may render retroviruses and retrovirus-like particles inactive, reducing unwanted viral activity of the mixture.

The reduction of viral activity in a mixture may be quantified by a reduction factor. A reduction factor may be calculated according to Equation 1, shown below, $$\text{Reduction Factor} = \log\left(\frac{V_1 \times C_1}{V_2 \times C_2}\right) \qquad \text{Eq. (1)}$$

where $V_1$ is the volume of the mixture before viral inactivation, $C_1$ is the viral concentration or infectious units per volume of the mixture before viral inactivation, $V_2$ is the volume of the mixture after viral inactivation, and $C_2$ is the viral concentration of the mixture after viral inactivation. In various embodiments of the present disclosure, including methods for viral inactivation, a reduction factor greater than or equal to 2.5 is achieved, such as, for example, a reduction factor greater than or equal to 3, greater than or equal to 3.5, greater than or equal to 4, greater than or equal to 4.5, or greater than or equal to 5. As used herein, "effective viral inactivation" may refer to viral inactivation associated with a reduction factor greater than or equal to 2.5, greater than or equal to 3, greater than or equal to 3.5, greater than or equal to 4, greater than or equal to 4.5, or greater than or equal to 5.

According to one or more embodiments, an acid addition amount may be calculated based on the protein concentration of the mixture and an inactivation pH. For example an acid addition amount may be calculated according to Equation 2, shown below, $$w = Ax + By + C \qquad \text{Eq. (2)}$$

where x is the protein concentration of the mixture in grams per liter (g/L), y is the inactivation pH, w is the acid addition amount in moles of acid per kilogram of mixture (mol/kg), and A, B, and C are constants. Constant A of Equation 2 has units of liter-moles of acid per gram-kilograms of mixture (L·mol/g·kg). Constant A may be greater than or equal to 0.0003 L·mol/g·kg and less than or equal to 0.0006 L·mol/g·kg, such as, for example, approximately 0.0003 L·mol/g·kg to approximately 0.0005 L·mol/g·kg, approximately 0.0004 L·mol/g·kg to approximately 0.0006 L·mol/g·kg, approximately 0.00035 L·mol/g·kg to approximately 0.0005 L·mol/g·kg, approximately 0.00035 L·mol/g·kg to approximately 0.0006 L·mol/g·kg or approximately 0.0004 L·mol/g·kg to approximately 0.00055 L·mol/g·kg. Constants B and C of Equation 2 have units of moles of acid per kilograms of mixture (mol/kg). Constant B may be greater than or equal to −0.1 mol/kg and less than or equal to 0 mol/kg, such as, for example, approximately −0.1 mol/kg to approximately 0 mol/kg, approximately −0.1 mol/kg to approximately −0.05 mol/kg, approximately −0.05 mol/kg to approximately 0 mol/kg, or approximately −0.08 mol/kg to approximately −0.01 mol/kg. Constant C may be greater than or equal to 0.02 mol/kg and less than or equal to 0.1 mol/kg, such as, for example, approximately 0.02 mol/kg to approximately 0.1 mol/kg, approximately 0.02 mol/kg to approximately 0.05 mol/kg, approximately 0.05 mol/kg to approximately 0.1 mol/kg, or approximately 0.04 mol/kg to approximately 0.08 mol/kg.

In some embodiments, an acid addition amount may be calculated based on the protein concentration of the mixture, an inactivation pH, and a pH of the mixture. For example, an acid addition amount may be calculated according to Equation 3, shown below, $$w = Ex + Fy + Gz + H \qquad \text{Eq. (3)}$$

where x is the protein concentration of the mixture in grams per liter (g/L), y is the inactivation pH, z is the mixture pH, w is the acid addition amount in moles of acid per kilogram of mixture (mol/kg), and E, F, G, and H are constants. Constant E of Equation 3 has units of liter-moles of acid per gram-kilograms of mixture ($L \cdot mol/g \cdot kg$) and constants F, G, and H have units of moles of acid per kilogram of mixture (ml/kg). Constant E may be greater than or equal to 0.00005 $L \cdot mol/g \cdot kg$ and less than or equal to 0.0005 $L \cdot mol/g \cdot kg$, such as, for example, approximately 0.00005 $L \cdot mol/g \cdot kg$ to approximately 0.0005 $L \cdot mol/g \cdot kg$, approximately 0.0001 $L \cdot mol/g \cdot kg$ to 0.0005 $L \cdot mol/g \cdot kg$, approximately 0.00005 $L \cdot mol/g \cdot kg$ to 0.00045 $L \cdot mol/g \cdot kg$, approximately 0.0001 $L \cdot mol/g \cdot kg$ to approximately 0.00035 $L \cdot mol/g \cdot kg$, or approximately 0.00035 $L \cdot mol/g \cdot kg$ to approximately 0.0005 $L \cdot mol/g \cdot kg$. Constant F may be greater than or equal to −0.2 mol/kg and less than or equal to 0 mol/kg, such as, for example, approximately −0.1 mol/kg to approximately 0 mol/kg, approximately −0.1 mol/kg to approximately −0.05 mol/kg, approximately −0.05 mol/kg to approximately 0 mol/kg, or approximately −0.08 mol/kg to approximately −0.01 mol/kg. Constant G may be greater than or equal to 0 mol/kg and less than or equal to 0.03 mol/kg, such as, for example, approximately 0 mol/kg to approximately 0.03 mol/kg, approximately 0.001 mol/kg to approximately 0.03 mol/kg, approximately 0.005 mol/kg to approximately 0.3 mol/kg, or approximately 0.005 mol/kg to approximately 0.025 mol/kg. Constant H may be a number greater than or equal to −0.1 mol/kg and less than or equal to 0.1 mol/kg, such as, for example, approximately −0.1 mol/kg to approximately 0.1 mol/kg, approximately −0.08 mol/kg to approximately 0.08 mol/kg, approximately −0.05 mol/kg to approximately 0.1 mol/kg, or approximately −0.1 mol/kg to approximately 0.05 mol/kg.

The specific equation that relates mixture protein concentration to acid addition amount and inactivation pH (that may, optionally, be dependent on mixture pH) may vary by target molecule and/or acid system used. The values of the constants defined above, as applied to a given target molecule and acid system, may be determined by regression according to the general equations defined above. As described in the example section below, the acid addition amount is unexpectedly found to have a strong correlation to mixture protein concentration according to the above defined equations. This unexpectedly strong correlation may allow for the general equations described herein and their derivatives to be incorporated into PAT.

In one or more embodiments, the acid addition amount is approximately 0.002 moles of acid per kilogram of mixture (mol/kg) to approximately 0.025 mol/kg, such as, for example, approximately 0.002 mol/kg to approximately 0.025 mol/kg, approximately 0.01 mol/kg to approximately 0.025 mol/kg, approximately 0.002 mol/kg to approximately 0.020 mol/kg, or approximately 0.005 mol/kg to approximately 0.020 mol/kg.

In some embodiments, after an acid addition amount is calculated, acid may be added to a mixture to bring the mixture to the inactivation pH. For example, in at least one embodiment, a bolus of acid, equivalent to the acid addition amount, may be added to the mixture to bring the pH of the mixture less than or equal to the inactivation pH. In other embodiments, a first portion of acid is added to the mixture, then subsequently, one or more additional portions of acid may be added to the mixture such that the pH of the mixture is at or below the inactivation pH. In such embodiments, the first portion of acid is 68% to 99% of the acid addition amount, such as, for example, approximately 75% to approximately 99%, approximately 80% to approximately 99%, approximately 85% to approximately 99%, approximately 90% to approximately 99%, approximately 85% to approximately 95%, or approximately 90% to approximately 99%.

The first portion of acid may be proportioned such that target molecule in a mixture with the lowest possible pH would not be denatured by the addition of the first portion. Additional portions of acid may include one or more additions of acid that occur after the addition of the first portion of acid, such as, for example, 3 additions of acid, 4 additions of acid, or 5 additions of acid that occur after the addition of the first portion of acid. Each addition of the one or more additions of acid may be in an amount that is 0.1% to 32% of the acid addition amount, such as, for example, approximately 0.1% to approximately 30%, approximately 0.1% to approximately 25%, approximately 0.1% to approximately 20%, approximately 1% to approximately 25%, approximately 0.1% to approximately 15%, approximately 0.1% to approximately 10%, approximately 1% to approximately 15%, approximately 1% to approximately 10%, or approximately 0.1% to approximately 5%. Each addition of the one or more additions of acid may be in the same amount as one or more other additions of acid. In other embodiments, each addition of acid is the same amount as each other addition of acid.

In some embodiments, a pH may be measured after the first portion of acid is added to the mixture, but prior to the addition of additional portions of acid. In some such embodiments, the pH of the mixture, as measured after the first portion of acid is added, is greater than or equal to 3.5 and less than or equal to 3.75, such as, for example, approximately 3.5 to approximately 3.75, approximately 3.6 to approximately 3.7, approximately 3.5 to approximately 3.65, approximately 3.6 to approximately 3.75, or approximately 3.5 to approximately 3.65. As used herein, a pH value, or a range of pH values, may have a variation of ±0.02 pH units.

Acid may be added in the form of one or more acidic solutions. The acidic solutions may include any suitable acid, such as, for example, HCl, HBr, $H_3PO_4$, $HO_2C_2O_2H$, $C_6H_8O_7$, $H_2SO_3$, $H_3PO_4$, $HNO_2$, $C_6H_5CO_2H$, $CH_3CO_2H$, HClO, HCN, $H_3BO_3$, or a combination thereof. In addition or alternatively, the acidic solutions may include one or more salts, such as, for example, glycine, arginine, sodium acetate, and/or sodium chloride.

After the acid addition amount is added to the mixture including the target molecule, the formed mixture has a pH that is at or below the inactivation pH. In some embodiments, the pH of the formed mixture may be measured, e.g., to confirm that it is within a desired range. As described previously, the mixture may be held at the inactivation pH for an inactivation interval. After the mixture is held at the inactivation pH for an inactivation interval, a reduction in viral activity may occur equivalent to a reduction factor of, for example, greater than or equal to 2.5, greater than or equal to 3, greater than or equal to 3.5, or greater than or equal to 4. After the mixture is held at the inactivation pH for the inactivation interval, the mixture may be titrated by adding an alkaline solution so that the pH of the mixture is greater than or equal to 4.5 and less than or equal to 8.5, such as, for example, greater than or equal to 4.5 and less than or equal to 8.5, greater than or equal to 5.0 and less than or equal to 8.5, greater than or equal to 5.8 and less than or equal to 8.5, greater than or equal to 5.9 and less than or equal to 8.5, greater than or equal to 6.0 and less than or equal to 8.5, greater than or equal to 6.1 and less than or equal to 8.5, greater than or equal to 6.2 and less than or equal to 8.5, greater than or equal to 6.3 and less than or equal to 8.5, or greater than or equal to 6.4 and less than or equal to 8.5. As used herein, a pH value, or a range of pH values, may have a variation of $\pm 0.02$ pH units. The alkaline solution may include one or more bases, such as, for example, NaOH, KOH, LiOH, $Ca(OH)_2$, $NH_4OH$, $NaCH_3CO_2$ and/or $(HOCH_2)_3CNH_2$.

In some embodiments, the mixture is titrated less than an hour after the first portion of acid is added, such as, for example, less than approximately 50 minutes, less than approximately 45 minutes, less than approximately 40 minutes, less than approximately 35 minutes, or less than approximately 30 minutes after the first portion of acid is added.

Aspects of the present disclosure may also include methods for determining a function predictive of the pH of the combination (i.e., combined mixture and acid). For example, a function may be determined that predicts combination pH (e.g., an inactivation pH) based on a measured protein concentration and/or pH of the mixture, and an amount of acid added to the mixture. Such a function can be used to detect a processing error (e.g., insufficient mixing, poor sampling, or the like) or a deficiency in equipment (instrumental error, instrument drift, pH probe malfunction, or the like).

In some embodiments, the expected pH of an acidified mixture may be predetermined according to a confirmation model. The confirmation model may be in the form of Equation 4, shown below, $$y=Kx+Lw+Mz+N \qquad \text{Eq. (4)}$$

where y is the inactivation pH, x is the protein concentration of the mixture in grams per liter (g/L), z is the mixture pH, w is the acid addition amount in moles of acid per kilogram of mixture (mol/kg), and K, L, M, and N are constants. Constant K of Equation 4 has units of liters per gram, constant L has units of kilogram of mixture per moles of acid, and constants M and N are unitless. Constant K may be greater than or equal to 0 L/g and less than or equal to 0.03 L/g, such as, for example, approximately 0 L/g to approximately 0.03 L/g, approximately 0.001 L/g to approximately 0.03 L/g, approximately 0 L/g to approximately 0.025 L/g, or approximately 0.001 L/g to approximately 0.025 L/g.

Constant L may be greater than or equal to $-80$ kg/mol and less than or equal to $-60$ kg/mol, such as, for example, approximately $-75$ kg/mol to approximately $-60$ kg/mol, approximately $-80$ kg/motto approximately $-65$ kg/mol, or approximately $-75$ kg/mol to approximately $-65$ kg/mol. Constant M may be greater than or equal to 0 and less than or equal to 2.0, such as, for example, approximately 0 to approximately 2.0, approximately 0.3 to approximately 2.0, approximately 0 to approximately 1.7, or approximately 0.3 to approximately 1.7. Constant N may be a number greater than or equal to $-1.0$ and less than or equal to 0, such as, for example, approximately $-1.0$ to approximately 0, approximately $-1.0$ to approximately $-0.1$, or approximately $-0.9$ to approximately $-0.1$.

In some embodiments, the pH and protein concentration of a mixture prior to the addition of acid may be measured and/or recorded. Based on the mixture pH, mixture protein concentration, and acid addition amount, an expected pH of the acidified mixture may be pre-determined using the confirmation model. An actual pH of the acidified mixture may be measured, recorded, and/or compared to the expected pH. Comparing the recorded pH to the expected pH may include calculating a difference (e.g., a percent difference) between the recorded pH and the expected pH.

In some embodiments, if the difference between the recorded pH and the expected pH is greater than a threshold amount, corrective action may be taken. A threshold amount may be, for example, $\pm 0.03$ pH from the expected pH, $\pm 0.05$ pH from the expected pH, $\pm 0.07$ pH from the expected pH, $\pm 0.09$ pH from the expected pH, $\pm 0.1$ pH from the expected pH, $\pm 0.15$ pH from the expected pH, or, $\pm 0.2$ pH from the expected pH. Corrective action may include, but is not limited to, adjusting a pH meter, adjusting the composition of the mixture, adjusting one or more environmental conditions of the process, or a combination thereof. Adjusting a pH meter may include standardizing, the pH meter, recalibrating the pH meter, cleaning, resetting, and/or replacing the pH probe, adjusting the reference electrode solution, replacing a part of the pH meter, adjusting the position of the pH probe, and/or other action which alters the signal to noise ratio of the pH meter. Adjusting the composition of the mixture may include reformulating any component solution of the mixture or upstream composition, altering process conditions or apparatus components of one or more chromatography or separation processes, and/or other action which alters the material composition of the mixture. Adjusting one or more environmental conditions of the process may include adjusting mixing and/or homogenizations processes and systems, adjusting a temperature of the process, adjusting a humidity of the process, adjusting a pressure of the process, or a combination thereof. Such adjustments based on deviation from expected parameters may be incorporated as part of PAT.

The equations and mathematical models described above may be generated as part of a method for developing an acidic inactivation protocol. The method for developing the acidic inactivation protocol may include producing a pool of mixtures (e.g., eluates), wherein each mixture of the pool contains a target molecule purified in a protein affinity capture process. For example, a pool of samples may be collected from the eluate of a protein affinity chromatography column. The method may further include measuring the pH and protein concentration (e.g., concentration of target molecule) of each sample. After the pH and protein concentration of each sample is determined, each sample may be titrated to determine an amount of acid needed to bring the sample to an inactivation pH. In some embodiments, inactivation pH may be defined as a broad enough range that two or more iterations of titration may be performed, allowing for the collection of multiple data points from each sample of the pool. In other embodiments, only a single data point may be collected from each sample.

In some embodiments, a relationship (e.g., a mathematical model) may be regressed between the amount of acid added, eluate protein concentration, mixture pH, and/or inactivation pH. The relationship may be regressed according to Equation 2 or Equation 3, as described above. In some embodiments, a method of developing an acidic inactivation protocol further comprises regressing a confirmation model. The confirmation model may be regressed according to Equation 4, described above.

FIG. 1 depicts, in flow-chart form, an exemplary process 100 for inactivating virus in a mixture, according to the present disclosure. According to step 101, a mixture at a first pH (e.g., greater than 3.9) may be eluted from a chromatography column. According to step 102, a protein concentration (e.g., target molecule concentration) of the mixture may be measured via, for example, ultraviolet/visible light spectroscopy or other method. Optionally, the conductivity and/or pH of the mixture may be measured via, for example, a potentiometric pH meter or other method. According to step 103, one or more salts may be added to the mixture in an amount sufficient to adjust the conductivity of the mixture. According to step 104, an amount of acid necessary to reduce the pH of the mixture to a second pH (e.g., an inactivation pH) may be calculated. This calculation may be performed on the basis of the protein concentration of the mixture, the pH of the mixture, or a combination thereof. According to step 105, a first portion of acid may be added to the mixture. In some embodiments, the first portion of acid is a bolus of acid equivalent to the calculated acid addition amount. In other embodiments, the first portion of acid may be 68% to 99% of the volume or amount of acid as the calculated acid addition amount. According to step 105, optionally, secondary acid may be added to the mixture such that the combination of mixture and acid is at or below the second pH (e.g., the inactivation pH). According to step 106, the combination of mixture and acid may be maintained at the second pH (e.g., the inactivation pH) for an inactivation interval, inactivating virus in the eluate. In some embodiments, FIG. 2 depicts, in flow-chart form, an exemplary process 200 for inactivating virus in a mixture, according to the present disclosure. According to step 201, a mixture including a target molecule may be loaded on a chromatography column at a first pH (e.g., greater than or equal to approximately 5.0 and less than or equal to approximately 8.5). According to step 202, an eluted mixture at a second pH (e.g., greater than approximately 3.9 and less than or equal to approximately 5.0) may be eluted from the chromatography column. According to step 203, a protein concentration (e.g., target molecule concentration) of the eluted mixture may be measured via, for example, ultraviolet/visible light spectroscopy and/or recorded. According to step 204, optionally, the pH and/or conductivity of the eluted mixture may be measured. The pH may be measured via, for example, potentiometric pH meter and/or recorded. According to step 205, one or more salts may be added to the mixture in an amount sufficient to adjust the conductivity of the mixture. According to step 206, acid may be added to the eluted mixture, forming a combination of the eluted mixture and acid, such that the combination is configured to demonstrate effective viral inactivation. Further, the combination may have a pH less than or equal to the second pH (e.g., less than or equal to approximately 3.8 and greater than or equal to approximately 3.0). According to step 207, an expected pH of the combination may be pre-determined using a pH confirmation model. According to step 208, the pH of the combination may be measured and/or recorded. According to step 209, a difference between the expected pH and the measured/recorded pH of the combination may be calculated. According to step 210, a corrective action may be taken based on the calculated difference between expected pH and the measured and/or recorded pH of the combination.

FIG. 3 depicts, in flow-chart form, an exemplary process 300 for developing an acidic inactivation protocol, according to the present disclosure. According to step 301, a pool of eluate samples may be produced, wherein each eluate sample of the pool of eluate samples contains a target molecule purified in an affinity capture process. According to step 302, a protein concentration (e.g., target molecule concentration) of each eluate samples of the pool of eluate samples may be measured via, for example, ultraviolet/visible light spectroscopy. Optionally, the pH of each eluate sample of the pool of eluate samples may be measured via, for example, potentiometric pH meter. According to step 303, an amount of acid necessary to reduce the pH of each eluate sample to an inactivation pH may be determined by titrating each eluate sample of the pool of eluate samples. According to step 304, a relationship between the amount of acid added, the eluate protein concentration, the eluate pH, and/or the inactivation pH may be regressed. According to step 305, optionally, a confirmation model also may be regressed.

Although each of FIGS. 1-3 depicts a specific order of steps, it is to be understood that the steps performed, and the order in which they are performed, may be modified. Additionally, steps (e.g., one or more of the measuring and/or recording steps) may be added or removed from any of the methods disclosed herein. Further, although each of FIGS. 1-3 depicts steps in relation to an eluate, it is to be understood that the steps may be applicable to any mixture containing a target molecule.

EXAMPLES

The following examples are intended to illustrate the present disclosure without being limiting in nature. It is understood that the present disclosure encompasses additional aspects and embodiments consistent with the foregoing description and following examples.

In the following examples, a target polypeptide was prepared from a mixture including the target polypeptide, host cell protein, viruses, and other contaminants, impurities, and components. The target polypeptide was prepared in Chinese Hamster Ovary cells grown in a suspension culture.

Example 1

The target polypeptide was eluted from a protein A affinity column and multiple samples of a mixture were obtained. The protein concentration of each mixture sample was obtained by ultraviolet/visible spectroscopy and is shown in Table 1, below, in units of grams of protein per liter of mixture. Additionally, the pH each mixture sample was measured and is shown in Table 1.

The pool of eluates included forty eluate samples (i.e., forty samples of the mixture) and each sample was titrated to an inactivation pH of 3.35 to 3.86 with a 0.25M solution of phosphoric acid ($H_3PO_4$) to determine an acid addition amount (e.g., an amount of acid that would need to be added to bring the mixture to the inactivation pH). For six of the forty samples (Samples 1-6, shown in Table 1), the titration was performed in multiple iterations to produce multiple data points. For example, 30.89 grams of acid per kilogram of mixture bringing Sample No. 1 to an inactivation pH of 3.70 is one data point, and when 5.35 additional grams of acid per kilogram of mixture are added, 36.24 grams of acid per kilogram of mixture bringing Sample No. 1 to an inactivation pH of 3.59 is another data point. The data for these titrations in shown in Table 1, below, with the acid addition amount shown in units of grams of acid per kilogram of mixture and moles of acid per kilogram of mixture.

TABLE 1

| | | Mixture Titration Data | | | |
|---|---|---|---|---|---|
| Sample No. | Mixture Protein Concentration (g/L) | Mixture pH | In-activation pH | Acid Addition Amount (g/kg) | Acid Addition Amount (mol/kg) |
| 1 | 17.6 | 4.25 | 3.70 | 30.89 | 0.007723 |
| 1 | 17.6 | 4.25 | 3.59 | 36.24 | 0.009060 |
| 2 | 17.3 | 4.23 | 3.86 | 22.75 | 0.005688 |
| 2 | 17.3 | 4.23 | 3.74 | 28.15 | 0.007038 |
| 2 | 17.3 | 4.23 | 3.63 | 33.20 | 0.008300 |
| 3 | 18.7 | 4.30 | 3.81 | 27.23 | 0.006808 |
| 3 | 18.7 | 4.30 | 3.67 | 33.39 | 0.008348 |
| 3 | 18.7 | 4.30 | 3.53 | 39.17 | 0.009793 |
| 4 | 15.0 | 4.24 | 3.84 | 21.96 | 0.005490 |
| 4 | 15.0 | 4.24 | 3.68 | 29.00 | 0.007250 |
| 4 | 15.0 | 4.24 | 3.53 | 35.19 | 0.008798 |
| 5 | 15.5 | 4.23 | 3.74 | 27.78 | 0.006945 |
| 5 | 15.5 | 4.23 | 3.65 | 31.43 | 0.007858 |
| 6 | 13.9 | 4.23 | 3.76 | 25.10 | 0.006275 |
| 6 | 13.9 | 4.23 | 3.68 | 28.20 | 0.007050 |
| 6 | 13.9 | 4.23 | 3.63 | 30.20 | 0.007550 |
| 7 | 17.5 | 4.26 | 3.70 | 33.41 | 0.008353 |
| 8 | 15.5 | 4.17 | 3.43 | 38.00 | 0.009500 |
| 9 | 15.8 | 4.18 | 3.66 | 28.33 | 0.007083 |
| 10 | 15.4 | 4.20 | 3.70 | 27.67 | 0.006918 |
| 11 | 15.3 | 4.18 | 3.54 | 32.67 | 0.008168 |
| 12 | 7.11 | 4.04 | 3.8 | 11.75 | 0.002938 |
| 13 | 7.28 | 4.04 | 3.39 | 24.67 | 0.006168 |
| 14 | 15.6 | 4.17 | 3.68 | 27.50 | 0.006875 |
| 15 | 7.31 | 4.01 | 3.69 | 14.67 | 0.003668 |
| 16 | 7.30 | 4.05 | 3.41 | 25.00 | 0.006250 |
| 17 | 11.8 | 4.13 | 3.38 | 33.33 | 0.008333 |
| 18 | 15.4 | 4.14 | 3.45 | 38.00 | 0.009500 |
| 19 | 7.32 | 4.06 | 3.39 | 25.00 | 0.006250 |
| 20 | 7.33 | 4.06 | 3.51 | 20.33 | 0.005083 |
| 21 | 15.5 | 4.20 | 3.41 | 40.00 | 0.01000 |
| 22 | 7.34 | 4.06 | 3.69 | 15.00 | 0.003750 |
| 23 | 19.3 | 4.35 | 3.53 | 46.00 | 0.01150 |
| 24 | 14.3 | 4.30 | 3.72 | 31.00 | 0.007750 |
| 25 | 8.76 | 4.22 | 3.41 | 33.67 | 0.008418 |
| 26 | 18.7 | 4.36 | 3.45 | 50.33 | 0.01258 |
| 27 | 18.6 | 4.37 | 3.42 | 51.67 | 0.01292 |
| 28 | 13.9 | 4.27 | 3.56 | 36.42 | 0.009105 |
| 29 | 8.67 | 4.22 | 3.4 | 33.33 | 0.008333 |
| 30 | 6.88 | 4.21 | 3.64 | 25.83 | 0.006458 |
| 31 | 8.70 | 4.23 | 3.57 | 28.58 | 0.007145 |
| 32 | 8.69 | 4.20 | 3.70 | 23.83 | 0.005958 |
| 33 | 8.68 | 4.21 | 3.41 | 33.75 | 0.008438 |
| 34 | 8.86 | 4.21 | 3.71 | 24.33 | 0.006083 |
| 35 | 18.4 | 4.33 | 3.72 | 37.08 | 0.009270 |
| 36 | 8.73 | 4.21 | 3.41 | 33.75 | 0.008438 |
| 37 | 18.6 | 4.35 | 3.76 | 35.67 | 0.008918 |
| 38 | 18.6 | 4.37 | 3.39 | 53.33 | 0.01333 |
| 39 | 8.74 | 4.22 | 3.55 | 29.33 | 0.007333 |
| 40 | 7.34 | 4.05 | 3.35 | 25.00 | 0.006250 |

Example 2

The titration data shown in Table 1 was used to regress a relationship between mixture protein concentration, inactivation pH, and acid addition amount, according to Equation 2. The regressed equation (Equation 5), shown below, was determined to have a coefficient of determination ($R^2$) of 0.84.

$$w=0.0004532x-0.01135y+0.04213 \qquad \text{Eq. (5)}$$

Example 3

Still referring to the titration data shown in Table 1, a relationship was regressed between mixture protein concentration, mixture pH, inactivation pH, and acid addition amount, according to Equation 3. The regressed equation (Equation 6), shown below, was determined to have a coefficient of determination ($R^2$) of 0.97. Unexpectedly, acid addition amount was highly correlated to the relationship between protein concentration, mixture pH, and inactivation pH shown in the general Equations 2 and 3.

$$w=0.0001986x-0.01162y+0.01510z-0.01692 \qquad \text{Eq. (6)}$$

Example 4

The titration data shown in Table 1 was also used to regress a confirmation model according to general Equation 4. The regressed equation (Equation 7), shown below, was determined to have a coefficient of determination ($R^2$) of 0.93. Also unexpectedly, the inactivation pH was highly correlated to the relationship between protein concentration, mixture pH, and inactivation pH.

$$y=0.01488x-71.65w+1.094z-0.6727 \qquad \text{Eq. (7)}$$

Those skilled in the art will appreciate that the conception upon which this disclosure is based may readily be used as a basis for designing other methods and systems for carrying out the several purposes of the present disclosure. Additionally, while aspects of the present disclosure are described with respect to particular steps in particular processes (e.g., viral inactivation in a mixture), one of skill in the art will appreciate that the systems and methods disclosed herein may be applicable in other contexts (e.g., viral inactivation in other mixtures including a polypeptide, such as before a chromatography process or after combination of an eluate with further ingredients in the process of making a formulated drug substance). Accordingly, the claims are not to be considered as limited by the foregoing description.

What is claimed is:

1. A method for inactivating virus in a mixture, the method comprising:

eluting, from a chromatography column, the mixture at a pH greater than 3.9 and less than 8.5;

measuring a protein concentration of the mixture;

based on the protein concentration of the mixture, calculating an amount of acid necessary to reduce the pH of the mixture to an inactivation pH;

adding a first portion of acid to the mixture, wherein the first portion of acid is 68% to 99% of the amount of acid necessary to reduce the pH of the mixture to the inactivation pH; and adding an additional portion of acid to the mixture such that the pH of the combination of mixture and acid is at or below the inactivation pH.

2. The method of claim 1, further comprising:

maintaining the combination at the inactivation pH for an inactivation interval; and after the inactivation interval, titrating the combination to a pH greater than or equal to 4.5 and less than or equal to 8.5, wherein the combination is titrated less than an hour after the first portion of acid is added to the mixture.

3. The method of claim 1, further comprising measuring a pH of the mixture prior to adding the first portion of acid to the mixture.

4. The method of claim 3, wherein the amount of acid necessary to reduce the pH of the mixture to the inactivation pH is calculated according to the following equation:

$$w=Ax+By+C$$

wherein w is the amount of acid in moles of acid per kilogram of mixture, x is the protein concentration of the mixture in grams per liter, y is the inactivation pH, and A, B, and C are constants.

5. The method of claim 4, wherein:

A is greater than or equal to approximately 0.0003 L·mol/g·kg and less than or equal to approximately 0.0006 L·mol/g·kg;

B is greater than or equal to approximately −0.1 mol/kg and less than or equal to approximately 0.0 mol/kg; and C is greater than or equal to approximately 0.02 and less than or equal to approximately 0.1.

6. The method of claim 3, wherein the amount of acid necessary to reduce the pH of the mixture to an inactivation pH is calculated based on the protein concentration of the mixture and the pH of the mixture.

7. The method of claim 1, wherein the amount of acid necessary to reduce the pH of the mixture to the inactivation pH is about 0.002 moles to about 0.025 moles of acid per kilogram of mixture.

8. The method of claim 1, wherein the inactivation pH is less than or equal to approximately 3.8 and greater than or equal to approximately 3.0.

9. The method of claim 1, further comprising:

measuring a conductivity of the mixture; and adding one or more salts to the mixture in an amount sufficient to adjust the conductivity of the mixture.

10. The method of claim 1, wherein the chromatography column is configured to perform a protein affinity capture process.

11. The method of claim 1, wherein, after the first portion of acid is added and prior to the addition of the additional portion of acid, the pH of the mixture is between approximately 3.5 and approximately 3.75.

12. A method for inactivating virus in a mixture, the method comprising:

loading a mixture including a target molecule on a chromatography column, the mixture having a pH greater than or equal to approximately 5.0 and less than or equal to approximately 8.5;

eluting, from the chromatography column, an eluted mixture including the target molecule, the eluted mixture having a pH greater than approximately 3.9 and less than or equal to approximately 5.0;

measuring a protein concentration of the eluted mixture;

adding an amount of acid to the eluted, forming a combination of the eluted mixture and acid, wherein the combination is configured to demonstrate effective viral inactivation and the combination has a pH less than or equal to approximately 3.8 and greater than or equal to approximately 3.0;

using a pH confirmation model, pre-determining an expected pH of the combination based on the protein concentration of the eluted mixture;

recording a pH of the combination;

calculating a difference between the expected pH and the recorded pH; and based on the calculated difference between the expected pH and the recorded pH, taking a corrective action.

13. The method of claim 12, wherein the corrective action is taken if the difference between the expected pH and the recorded pH is greater than or equal to approximately 0.15.

14. The method of claim 12, wherein the corrective action includes adjusting a pH meter, adjusting a composition of the mixture, adjusting one or more environmental conditions, or a combination thereof.

15. The method of claim 12, wherein the combination is kept at a pH less than or equal to approximately 3.8 and greater than or equal to approximately 3.0 for approximately 30 minutes.

16. The method of claim 12, further comprising:

titrating the combination to a pH greater than or equal to approximately 4.5 and less than or equal to approximately 8.5, less than an hour after adding the amount of acid to the mixture.

17. The method of claim 12, further comprising:

measuring a conductivity of the mixture; and adding one or more salts to the mixture in an amount sufficient to adjust the conductivity of the mixture.

18. The method of claim 12, further comprising:

measuring a pH of the mixture prior to adding the amount of acid to the mixture.

19. The method of claim 12, wherein the pH confirmation model includes the following equation:

$$y=Kx+Lw+Mz+N$$

where y is the pH of the combination, x is the protein concentration of the mixture in grams per liter, z is the pH of the mixture prior to adding the amount of acid to the mixture, w is the amount of acid added to the mixture in moles of acid per kilogram of eluate, and K, L, M, and N are constants.

20. A method for inactivating virus in a mixture, the method comprising:

measuring a protein concentration of the mixture;

based on the protein concentration of the mixture, calculating an amount of acid necessary to reduce the pH of the mixture to an inactivation pH; and adding the amount of acid necessary to bring the pH of the mixture to the inactivation pH to the mixture.

21. The method of claim 20, further comprising pre-determining an expected pH of the mixture after the acid is added to the mixture, using a pH confirmation model.

22. The method of claim 21, further comprising:

recording a pH of the combination of acid and the mixture; and calculating a difference between the expected pH and the recorded pH; and based on the calculated difference between the expected pH and the recorded pH, taking a corrective action.

23. The method of claim 20, further comprising, before adding the amount of acid:

measuring a conductivity of the mixture; and adding one or more salts to the mixture in an amount sufficient to adjust the conductivity of the mixture.

24. The method of claim 1, wherein the mixture includes a monoclonal antibody with a molecular weight of 130 kDa to 200 kDa.

25. The method of claim 1, wherein the mixture includes a monoclonal antibody with a molecular weight of 126 kDa to 154 kDa.

26. The method of claim 12, wherein the target molecule is a monoclonal antibody with a molecular weight of 130 kDa to 200 kDa.

27. The method of claim 12, wherein the target molecule is a monoclonal antibody with a molecular weight of 126 kDa to 154 kDa.

28. The method of claim 20, wherein the mixture includes a monoclonal antibody with a molecular weight of 130 kDa to 200 kDa.

29. The method of claim 20, wherein mixture includes a monoclonal antibody with a molecular weight of 126 kDa to 154 kDa.

* * * * *